United States Patent
DeSousa et al.

(10) Patent No.: US 11,793,430 B2
(45) Date of Patent: Oct. 24, 2023

(54) USE OF ADDITIVES, COPOLYMERS, AND DOPANTS FOR OPTICAL STABILITY OF ANALYTE SENSING COMPONENTS

(71) Applicant: Senseonics, Incorporated, Germantown, MD (US)

(72) Inventors: Ryan DeSousa, Germantown, MD (US); Robert Atwood, Germantown, MD (US); Philip Huffstetler, Germantown, MD (US); Joon Chatterjee, Germantown, MD (US); Sanat Mohanty, Germantown, MD (US)

(73) Assignee: Senseonics, Incorporated, Germantown, MD (US)

(*) Notice: Subject to any disclaimer, the term of this patent is extended or adjusted under 35 U.S.C. 154(b) by 448 days.

(21) Appl. No.: 17/061,297

(22) Filed: Oct. 1, 2020

(65) Prior Publication Data
US 2021/0093235 A1     Apr. 1, 2021

Related U.S. Application Data

(60) Provisional application No. 62/908,904, filed on Oct. 1, 2019.

(51) Int. Cl.
*A61B 5/145* (2006.01)
*A61B 5/1455* (2006.01)

(52) U.S. Cl.
CPC ........ *A61B 5/14546* (2013.01); *A61B 5/1455* (2013.01)

(58) Field of Classification Search
CPC ... A61B 5/145; A61B 5/1455; A61B 5/14551; A61B 5/14532; A61B 5/14546; A61B 5/14503; A61B 5/1451; A61B 5/1459; A61B 5/6861; A61B 2562/0233
See application file for complete search history.

(56) References Cited

U.S. PATENT DOCUMENTS

| | | | | |
|---|---|---|---|---|
| 3,714,114 | A * | 1/1973 | Stretanski | C08K 3/22 524/100 |
| 3,904,791 | A * | 9/1975 | Iverson | B44C 1/22 427/398.1 |
| 5,512,246 | A | 4/1996 | Russell et al. | |
| 5,517,313 | A | 5/1996 | Calvin, Jr. | |
| 8,419,985 | B2 * | 4/2013 | Miteva | B82Y 20/00 524/505 |
| 9,414,775 | B2 | 8/2016 | Calvin, Jr. et al. | |
| 9,693,714 | B2 | 7/2017 | DeHennis et al. | |
| 9,931,068 | B2 | 4/2018 | Huffstetler et al. | |
| 2013/0241745 | A1 | 9/2013 | Calvin, Jr. et al. | |
| 2014/0343381 | A1 * | 11/2014 | Whitehurst | A61B 5/1455 600/323 |
| 2017/0121590 | A1 * | 5/2017 | Lopez | C09K 8/035 |

* cited by examiner

*Primary Examiner* — Chu Chuan Liu
(74) *Attorney, Agent, or Firm* — Rothwell, Figg, Ernst & Manbeck, P.C.

(57) ABSTRACT

A sensor (e.g., an optical sensor) that may be implanted within a living animal (e.g., a human) and may be used to measure an analyte (e.g., glucose or oxygen) in a medium (e.g., interstitial fluid, blood, or intraperitoneal fluid) within the animal. The sensor may include a sensor substrate, electrode or housing, an analyte indicator covering at least a portion of the sensor, and one or more optical signal stabilizing additives in an environment of the sensor.

39 Claims, 7 Drawing Sheets

USE OF ADDITIVES, COPOLYMERS, AND DOPANTS FOR OPTICAL STABILITY OF ANALYTE SENSING COMPONENTS

CROSS-REFERENCE TO RELATED APPLICATION

The present application claims the benefit of priority to U.S. Provisional Application Ser. No. 62/908,904, filed on Oct. 1, 2019, which is incorporated herein by reference in its entirety.

BACKGROUND

Field of Invention

The present invention relates generally to sensors for implantation within a living animal and measurement of a concentration of an analyte in a medium within the living animal. Specifically, the present invention relates to sensors having a polymer graft including indicator molecules on the surface of the sensor body, where the opacity of the graft does not vary over time.

Discussion of the Background

A sensor may be implanted (partially or fully) within a living animal (e.g., a human) and used to measure the concentration of an analyte (e.g., glucose, oxygen, cardiac markers, low-density lipoprotein (LDL), high-density lipoprotein (HDL), or triglycerides) in a medium (e.g., interstitial fluid (ISF), blood, or intraperitoneal fluid) within the living animal. The sensor may include a light source (e.g., a light-emitting diode (LED) or other light emitting element), indicator molecules, and a photodetector (e.g., a photodiode, phototransistor, photoresistor or other photosensitive element). Examples of implantable sensors employing indicator molecules to measure an analyte are described in U.S. Pat. Nos. 5,517,313 and 5,512,246, which are incorporated herein by reference in their entirety.

A sensor may include an analyte indicator, which may be in the form of indicator molecules embedded in a graft (i.e., layer or matrix). For example, in an implantable fluorescence-based glucose sensor, fluorescent indicator molecules may reversibly bind glucose and, when irradiated with excitation light (e.g., light having a wavelength of approximately 378 nm), emit an amount of light (e.g., light in the range of 400 to 500 nm) that depends on whether glucose is bound to the indicator molecule.

If a sensor is implanted in the body of a living animal, the opacity of a graft may vary over time. A light source (e.g., light emitting diode (LED)) may emit the excitation light, which may then be absorbed by the indicator molecules in the polymer graft. A portion of the absorbed excitation light may be reflected from the polymer graft back into the sensor, and a portion of the absorbed excitation light may be emitted by the indicator molecules at a higher wavelength. The reflected and emitted light (e.g., fluorescent light) may be absorbed by one or more photodetectors within the body of the sensor. As the graft becomes less opaque, i.e., more clear, more excitation light may pass through the graft and less excitation light may be reflected off the graft and onto one or more photodetectors. Further, less fluorescence light may also be reflected off the graft and absorbed by one or more photodetectors.

Error may be introduced into analyte readings taken by a sensor as conditions of the sensor change over the life of the sensor and/or conditions or the sensing medium (e.g., protein concentrations in interstitial fluid) change over time. Thus, there is presently a need in the art for improvements to reduce the introduction of error into analyte readings when using a system including a sensor implanted (partially or fully) or inserted into the living animal. Also, there is a need in the art for continuous analyte sensors having increased reliable longevity.

SUMMARY

The present invention overcomes the disadvantages of prior systems by providing, among other advantages, reduced variation in the opacity of the polymer graft of a sensor that may result from changes in the sensing medium.

One aspect of the present invention provides a sensor that may be for placement within a living animal and for measurement of an analyte in a medium within the living animal. The sensor may include a sensor housing and a polymer graft covering at least a portion of the sensor housing. The polymer graft may include indicator molecules. The opacity of the graft may remain the same over time.

In some embodiments, the present disclosure may provide a sensor for measurement of an analyte in a medium within a living animal. The sensor may include an analyte indicator and one or more optical signal stabilizing additives. The analyte indicator may have an opacity. The one or more optical signal stabilizing additives may maintain the opacity of the analyte indicator over time.

In some embodiments, the one or more optical signal stabilizing additives may be selected from one or more of (a) titanium dioxide ($TiO_2$), (b) barium sulfate, magnesium silicate, (c) hollow beads, (d) solid beads, (e) monomers having vinyl functionality, and (f) dopants containing dithio groups. In some embodiments, the one or more optical signal stabilizing additives may have particle sizes of about 0.001 to about 100 μm.

In some embodiments, the one or more optical signal stabilizing additives may include hollow or solid beads. In some embodiments, the hollow or solid beads may be composed of one or more of: (a) silicon dioxide, (b) glass, (c) alumina, (d) melamine, and (e) polystyrene or polystyrene functionalized with one or more polyethylene glycols (PEGs), amino, carboxy-sulfate, sulfate, carboxylate, and hydroxylate moieties.

In some embodiments, the one or more optical signal stabilizing additives may include monomers having vinyl functionality. In some embodiments, the monomers may have vinyl functionality include hydrophobic vinyl monomers. In some embodiments, the monomers having vinyl functionality may include one or more of hydroxybutyl methacrylate, cyclohexyl methacrylate, hydroxypropyl methacrylate, and vinyl acetate.

In some embodiments, the one or more optical signal stabilizing additives may include one or more dithio-containing dopants ranging in alkyl chain length from 2-34 carbon atoms. In some embodiments, the one or more optical signal stabilizing additives may include 3,3'-dithiodipropionic acid. In some embodiments, the sensor may further include a sensor housing, and the analyte indicator may cover at least a portion of the sensor housing. In some embodiments, the sensor may further include a sensor substrate or a sensor electrode, and the analyte indicator may cover at least a portion of the sensor substrate or the sensor electrode.

In some embodiments, the sensor may be implantable within a living animal. In some embodiments, the one or more optical signal stabilizing additives may be co-monomers with the analyte indicator. In some embodiments, the one or more optical signal stabilizing additives may be co-monomers with the analyte indicator in a hydrogel. In some embodiments, the one or more optical signal stabilizing additives may be entrapped in a hydrogel covering at least a portion of the sensor housing.

In some embodiments, the analyte indicator may include a polymer including co-monomers of four monomers according to Formula V: A-B-C-D [Formula V], where A is an analyte indicator monomer, B is a methacrylate monomer, C is a polyethylene glycol monomer, and D is an optical signal stabilizing additive, A is 0.01 to 10% by weight, B is 1 to 99% by weight, C is 1 to 99% by weight, and D is 0.01 to 99% by weight of the total polymer.

In some embodiments, the analyte indicator may be configured to pass a percentage of light and configured such that the percentage of light passing through the analyte indicator would not change by more than 50% if the sensor were placed within the living animal for at least one month. In some embodiments, the percentage of light passing through the analyte indicator would not change by more than 20% if the sensor were placed within the living animal for at least one month. In some embodiments, the percentage of light passing through the analyte indicator would not change by more than 10% if the sensor were placed within the living animal for at least one month. In some embodiments, the percentage of light passing through the analyte indicator would not change by more than 50% if the sensor were placed within the living animal for at least two months. In some embodiments, the percentage of light passing through the analyte indicator would not change by more than 50% if the sensor were placed within the living animal for at least six months.

In some embodiments, the analyte indicator may be a polymer hydrogel including acrylic acid. In some embodiments, the analyte indicator may include polyethylene glycol monomers. In some embodiments, the analyte indicator may be made of a polymer hydrogel including polyethylene glycol monomers. In some embodiments, the sensor may further include a layer of platinum on an outside surface of the analyte indicator. In some embodiments, the platinum layer may be sputtered on the analyte indicator.

In some embodiments, the present disclosure may provide a method of fabricating a sensor for measurement of an analyte in a medium within a living animal. The method include applying an analyte indicator to a sensor such that the applied analyte indicator covers at least a portion of a sensor housing, sensor substrate, or sensor electrode. The analyte indicator may include one or more optical signal stabilizing additives, and the one or more optical signal stabilizing additives may maintain the opacity of the analyte indicator over time.

In some embodiments, the one or more optical signal stabilizing additives may be hollow or solid beads. In some embodiments, the hollow or solid beads may be composed of one or more of: (a) silicon dioxide, (b) glass, (c) alumina, (d) melamine, and (e) polystyrene or polystyrene functionalized with one or more polyethylene glycols (PEGs), amino, carboxy-sulfate, sulfate, carboxylate, and hydroxylate moieties.

In some embodiments, the one or more optical signal stabilizing additives may include monomers having vinyl functionality. In some embodiments, the monomers having vinyl functionality may include hydrophobic vinyl monomers. In some embodiments, the monomers having vinyl functionality may include one or more of hydroxybutyl methacrylate, cyclohexyl methacrylate, hydroxypropyl methacrylate, and vinyl acetate.

In some embodiments, the one or more optical signal stabilizing additives may include one or more dithio-containing dopants ranging in alkyl chain length from 2-34 carbon atoms. In some embodiments, the one or more optical signal stabilizing additives may include 3,3'-dithiodipropionic acid.

Further variations encompassed within the systems and methods are described in the detailed description of the invention below. Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION

While aspects of the subject matter of the present disclosure may be embodied in a variety of forms, the following description and accompanying drawings are merely intended to disclose some of these forms as specific examples of the subject matter encompassed by the present disclosure. Accordingly, the subject matter of this disclosure is not intended to be limited to the forms or aspects so described and illustrated.

As used herein, the terms "substantially" and "substantial" refer to a considerable degree or extent. When used in conjunction with, for example, an event, circumstance, characteristic, or property, the terms can refer to instances in which the event, circumstance, characteristic, or property occurs precisely as well as instances in which the event, circumstance, characteristic, or property occurs to a close approximation, such as accounting for typical tolerance levels or variability of the examples described herein.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one aspect, the degree of flexibility can be within about ±10% of the numerical value. In another aspect, the degree of flexibility can be within about ±5% of the numerical value. In a further aspect, the degree of flexibility can be within about ±2%, ±1%, or ±0.05%, of the numerical value.

Generally herein, the term "or" includes "and/or."

As used herein, a plurality of elements or steps may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Figure 1:
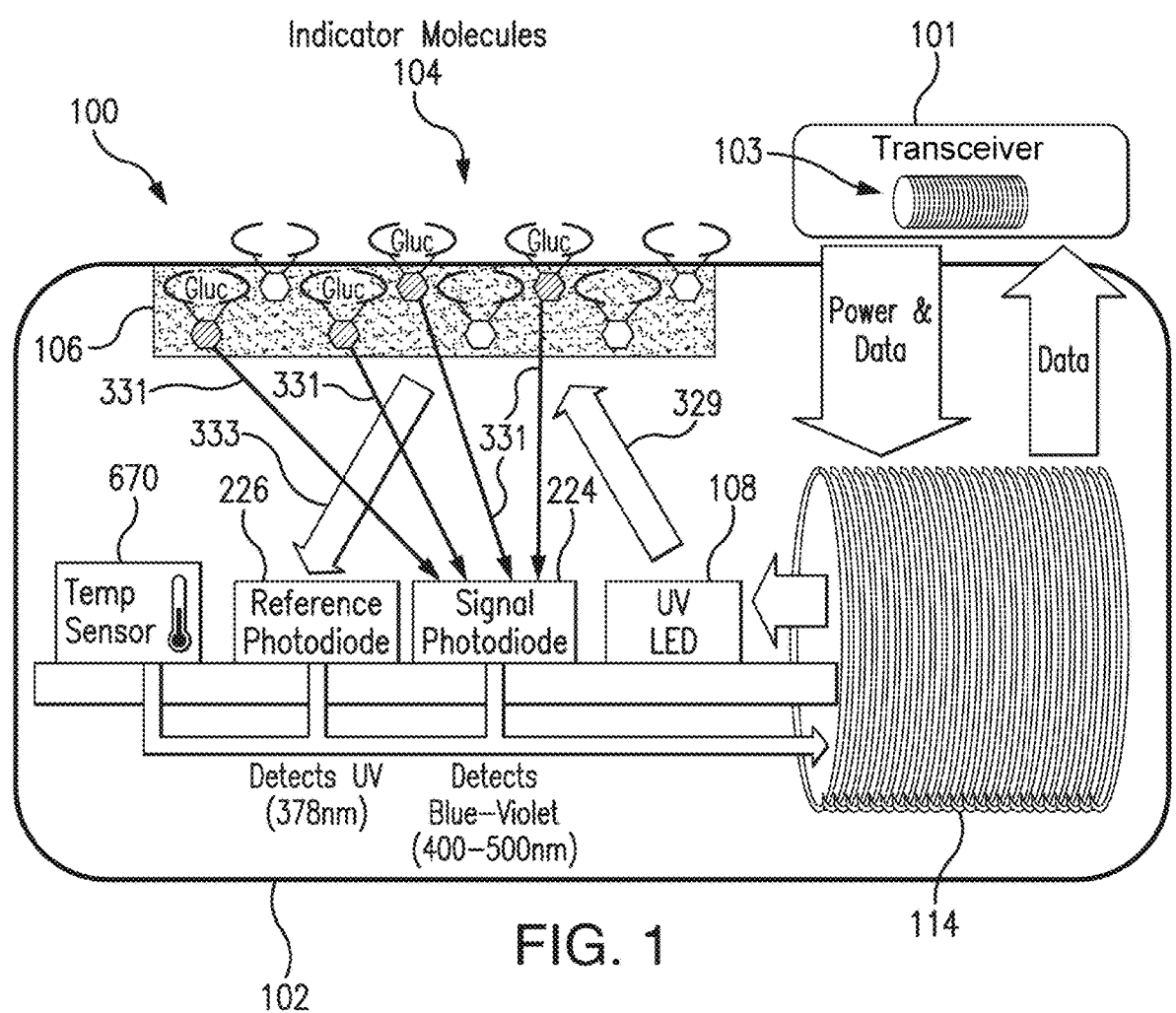
FIG. 1 is a schematic view illustrating a sensor system embodying aspects of the present invention.

FIG. 1 is a schematic view of a sensor system embodying aspects of the present invention. In some non-limiting embodiments, as shown in FIG. 1, the system may include a sensor 100 and an external transceiver 101. In some embodiments, the sensor 100 may be an implantable sensor configured to be fully or partially implanted in a living animal (e.g., a living human). The sensor 100 may be implanted, for example, in a living animal's arm, wrist, leg, abdomen, peritoneum, or other region of the living animal suitable for sensor implantation. For example, in some non-limiting embodiments, the sensor 100 may be implanted beneath the skin (i.e., in the subcutaneous or peritoneal tissues). However, this is not required, and, in some alternative embodiments, the sensor 100 may be a transcutaneous sensor.

In some embodiments, a transceiver 101 may be an electronic device that communicates with the sensor 100 to power the sensor 100, provide commands and/or data to the sensor 100, and/or receive data from the sensor 100. In some embodiments, the received data may include one or more sensor measurements. In some embodiments, the sensor measurements may include, for example and without limitation, one or more light measurements from one or more photodetectors of the sensor 100 and/or one or more temperature measurements from one or more temperature sensors of the sensor 100. In some embodiments, the transceiver 101 may calculate analyte (e.g., glucose) concentrations from the measurement information received from the sensor 100.

In some non-limiting embodiments, the transceiver 101 may be a handheld device or an on-body/wearable device. For example, in some embodiments where the transceiver 101 is an on-body/wearable device, the transceiver 101 may be held in place by a band (e.g., an armband or wristband) and/or adhesive, and the transceiver 101 may convey (e.g., periodically, such as every two minutes, and/or upon user initiation) measurement commands (i.e., requests for measurement information) to the sensor 100. In some embodiments where the transceiver 101 is a handheld device, positioning (i.e., hovering or swiping/waving/passing) the transceiver 101 within range over the sensor implant site (i.e., within proximity of the sensor 100) may cause the transceiver 101 to automatically convey a measurement command to the sensor 100 and receive a data from the sensor 100.

In some embodiments, as shown in FIG. 1, the transceiver 101 may include an inductive element 103, such as, for example, a coil. In some embodiments, the transceiver 101 may generate an electromagnetic wave or electrodynamic field (e.g., by using a coil) to induce a current in an inductive element 114 of the sensor 100. In some non-limiting embodiments, the sensor 100 may use the current induced in the inductive element 114 to power the sensor 100. However, this is not required, and, in some alternative embodiments, the sensor 100 may be powered by an internal power source (e.g., a battery).

In some embodiments, the transceiver 101 may convey data (e.g., commands) to the sensor 100. For example, in some non-limiting embodiments, the transceiver 101 may convey data by modulating the electromagnetic wave generated by the inductive element 103 (e.g., by modulating the current flowing through the inductive element 103 of the transceiver 101). In some embodiments, the sensor 100 may detect/extract the modulation in the electromagnetic wave generated by the transceiver 101. Moreover, the transceiver 101 may receive data (e.g., one or more sensor measurements) from the sensor 100. For example, in some non-limiting embodiments, the transceiver 101 may receive data by detecting modulations in the electromagnetic wave generated by the sensor 100, e.g., by detecting modulations in the current flowing through the inductive element 103 of the transceiver 101.

In some embodiments, as shown in FIG. 1, the sensor 100 may include a sensor housing 102 (i.e., body, shell, capsule, or encasement), which may be rigid and biocompatible. In exemplary embodiments, sensor housing 102 may be formed from a suitable, optically transmissive polymer material, such as, for example, acrylic polymers (e.g., polymethylmethacrylate (PMMA)).

In some embodiments, as shown in FIG. 1, the sensor 100 may include an analyte indicator 106. In some non-limiting embodiments, the analyte indicator 106 may be a polymer graft coated, diffused, adhered, or embedded on at least a portion of the exterior surface of the sensor housing 102. The analyte indicator 106 (e.g., polymer graft) may cover the entire surface of sensor housing 102 or only one or more portions of the surface of housing 102. As an alternative to coating the analyte indicator 106 on the outer surface of sensor housing 102, the analyte indicator 106 may be disposed on the outer surface of the sensor housing 102 in other ways, such as by deposition or adhesion. In some embodiments, the analyte indicator 106 may be a fluorescent glucose indicating polymer. In one non-limiting embodiment, the polymer is biocompatible and stable, grafted onto the surface of sensor housing 102, designed to allow for the direct measurement of glucose in interstitial fluid (ISF), blood, or intraperitoneal fluid after implantation of the sensor 100. In some embodiments, the analyte indicator 106 may comprise a hydrogel.

In some embodiments, the analyte indicator 106 (e.g., polymer graft) of the sensor 100 may include indicator molecules 104. The indicator molecules 104 may be distributed throughout the entire analyte indicator 106 or only throughout one or more portions of the analyte indicator 106. The indicator molecules 104 may be fluorescent indicator molecules (e.g., TFM having the chemical name 9-[N-[6-(4,4,5,5,-tetramethyl-1,3,2-dioxaborolano)-3-(trifluoromethyl)benzyl]-N-[3-(methacrylamido)propylamino]methyl]-10-[N-[6-(4,4,5,5,-tetramethyl-1,3,2-dioxaborolano)-3-(trifluoromethyl)benzyl]-N-[2-(carboxyethyl) amino]methyl]anthracene sodium salt) or light absorbing, non-fluorescent indicator molecules. In some embodiments, the indicator molecules 104 may reversibly bind an analyte (e.g., glucose, oxygen, cardiac markers, low-density lipoprotein (LDL), high-density lipoprotein (HDL), or triglycerides). When an indicator molecule 104 has bound an analyte, the indicator molecule may become fluorescent, in which case the indicator molecule 104 is capable of absorbing (or being excited by) excitation light 329 and emitting light 331. In one non-limiting embodiment, the excitation light 329 may have a wavelength of approximately 378 nm, and the emission light 331 may have a wavelength in the range of 400 nm to 500 nm. When no analyte is bound, the indicator molecule 104 may be only weakly fluorescent.

In some embodiments, the sensor 100 may include a light source 108, which may be, for example, a light emitting diode (LED) or other light source that emits radiation, including radiation over a range of wavelengths that interact with the indicator molecules 104. In other words, the light source 108 may emit the excitation light 329 that is absorbed by the indicator molecules in the matrix layer/polymer 104. As noted above, in one non-limiting embodiment, the light source 108 may emit excitation light 329 at a wavelength of approximately 378 nm.

In some embodiments, the sensor 100 may also include one or more photodetectors (e.g., photodiodes, phototransistors, photoresistors or other photosensitive elements). For example, in the embodiment illustrated in FIG. 1, sensor 100 has a first photodetector 224 and a second photodetector 226. However, this is not required, and, in some alternative embodiments, the sensor 100 may only include the first photodetector 224. In the case of a fluorescence-based sensor, the one or more photodetectors may be sensitive to fluorescent light emitted by the indicator molecules 104 such that a signal is generated by a photodetector (e.g., photodetector 224) in response thereto that is indicative of the level of fluorescence of the indicator molecules and, thus, the amount of analyte of interest (e.g., glucose).

Some part of the excitation light 329 emitted by the light source 108 may be reflected from the analyte indicator 106 back into the sensor 100 as reflection light 333, and some part of the absorbed excitation light may be emitted as emitted (fluoresced) light 331. In one non-limiting embodiment, the emitted light 331 may have a different wavelength than the wavelength of the excitation light 329. The reflected light 333 and emitted (fluoresced) light 331 may be absorbed by the one or more photodetectors (e.g., first and second photodetectors 224 and 226) within the body of the sensor 100.

Each of the one or more photodetectors may be covered by a filter 112 (see FIG. 3) that allows only a certain subset of wavelengths of light to pass through. In some embodiments, the one or more filters 112 may be thin glass filters. In some embodiments, the one or more filters 112 may be thin film (e.g., dichroic) filters deposited on the glass and may pass only a narrow band of wavelengths and otherwise reflect most of the received light. In some embodiments, the filters may be thin film (dichroic) filters deposited directly onto the photo detectors and may pass only a narrow band of wavelengths and otherwise reflect most of the light received thereby. The filters 112 may be identical (e.g., both filters 112 may allow signals to pass) or different (e.g., one filter 112 may be a reference filter and another filter 112 may be a signal filter).

In one non-limiting embodiment, the second (reference) photodetector 226 may be covered by a reference photodiode filter that passes light at the same wavelength as is emitted from the light source 108 (e.g., 378 nm). The first (signal) photodetector 224 may detect the amount of fluoresced light 331 that is emitted from the molecules 104 in the analyte indicator 106. In one non-limiting embodiment, the peak emission of the indicator molecules 104 may occur around 435 nm, and the first photodetector 224 may be covered by a signal filter that passes light in the range of about 400 nm to 500 nm. In some embodiments, higher glucose levels/concentrations correspond to a greater amount of fluorescence of the molecules 104 in the analyte indicator 106, and, therefore, a greater number of photons striking the first photodetector 224.

In some embodiments, as shown in FIG. 1, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/ or other electronic components, may be fabricated in the semiconductor substrate 116 with the remainder of the circuitry is secured to the semiconductor substrate 116, which may provide communication paths between the various secured components.

In some embodiments, the one or more of the sensor housing 102, analyte indicator 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

In some embodiments, the sensor 100 may include a transceiver interface device, and the transceiver 101 may include a sensor interface device. In some embodiments where the sensor 100 and transceiver 101 include an antenna or antennas (e.g., inductive elements 103 and 114), the transceiver interface device may include the inductive element 114 of the sensor 100, and the sensor interface device may include the inductive element 103 of the transceiver 101. In some of the transcutaneous embodiments where there exists a wired connection between the sensor 100 and the transceiver 101, the transceiver interface device and sensor interface device may include the wired connection.

Figure 2:
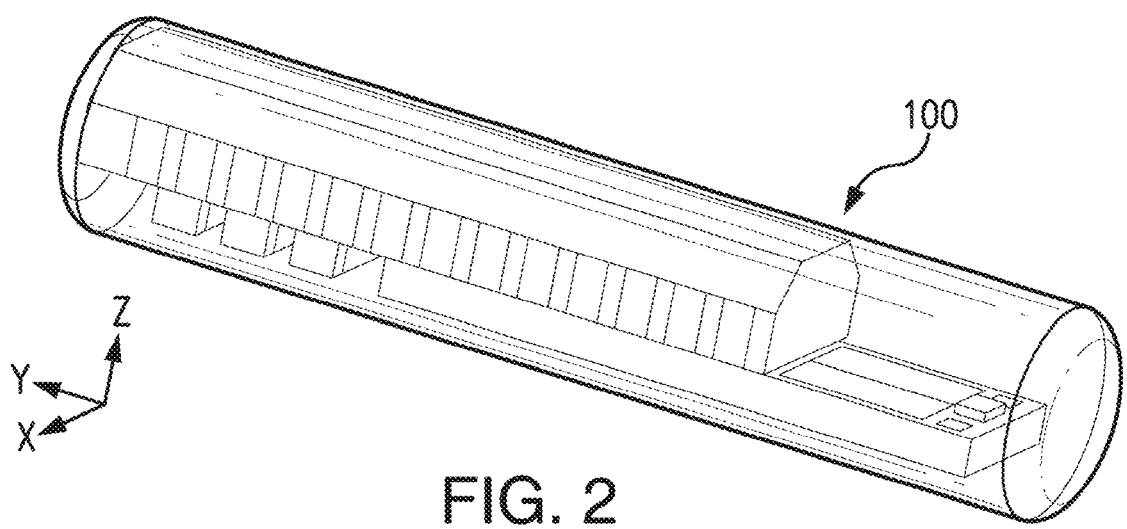
FIG. 2 illustrates a perspective view of a sensor embodying aspects of the present invention.
Figure 3:
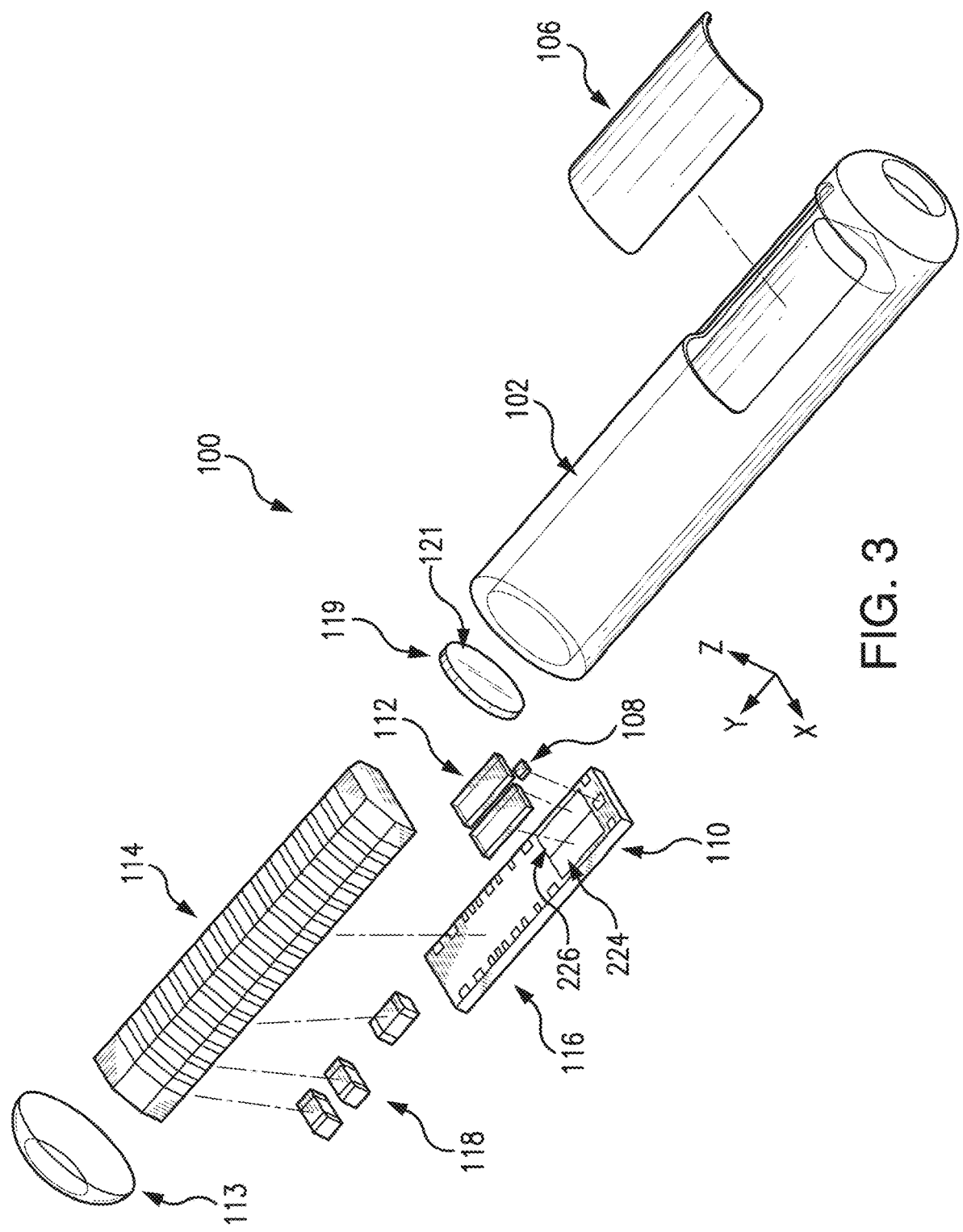
FIG. 3 illustrates an exploded view of a sensor embodying aspects of the present invention.

FIGS. 2 and 3 illustrate a non-limiting embodiment of a sensor 100 embodying aspects of the present invention that may be used in the sensor system illustrated in FIG. 1. FIGS. 2 and 3 illustrate perspective and exploded views, respectively, of the non-limiting embodiment of the sensor 100.

In some embodiments, as illustrated in FIG. 3, the sensor housing 102 may include an end cap 113. In some embodiments, the sensor 100 may include one or more capacitors 118. The one or more capacitors 118 may be, for example, one or more tuning capacitors and/or one or more regulation capacitors. The one or more capacitors 118 may be too large for fabrication in the semiconductor substrate 116 to be practical. Further, the one or more capacitors 118 may be in addition to one or more capacitors fabricated in the semiconductor substrate 116.

In some embodiments, as illustrated in FIG. 3, the sensor 100 may include a reflector 119 (i.e., mirror). Reflector 119 may be attached to the semiconductor substrate 116 at an end thereof. In a non-limiting embodiment, reflector 119 may be attached to the semiconductor substrate 116 so that a face portion 121 of reflector 119 is generally perpendicular to a top side of the semiconductor substrate 116 (i.e., the side of semiconductor substrate 116 on or in which the light source 108 and one or more photodetectors 110 are mounted or fabricated) and faces the light source 108. The face 121 of the reflector 119 may reflect radiation emitted by light source 108. In other words, the reflector 119 may block radiation emitted by light source 108 from exiting the axial end of the sensor 100.

According to one aspect of the invention, an application for which the sensor 100 was developed (although by no means the only application for which it is suitable) is measuring various biological analytes in the living body of an animal (including a human). For example, sensor 100 may be used to measure glucose, oxygen, toxins, pharmaceuticals or other drugs, hormones, and other metabolic analytes in, for example, the human body.

In some embodiments, the specific composition of the analyte indicator 106 and the indicator molecules 104 may vary depending on the particular analyte the sensor is to be used to detect and/or where the sensor is to be used to detect the analyte (e.g., in the in subcutaneous tissues, blood, or peritoneum). In some embodiments, the analyte indicator 106 facilitates exposure of the indicator molecules 104 to the analyte. In some embodiments, the indicator molecules 104 may exhibit a characteristic (e.g., emit an amount of fluorescence light) that is a function of the concentration of the specific analyte to which the indicator molecules 104 are exposed.

In some embodiments, the sensor 100 may include at least one drug eluting polymer matrix and/or a layer of catalyst and/or one or more therapeutic agents that may be provided on, adjacent to, incorporated in, or dispersed within the analyte indicator or sensor housing as described in U.S. Pat. No. 9,931,068 (Huffstetler et al.), which is incorporated herein by reference in its entirety. In some embodiments, the one or more therapeutic agents may be incorporated in the analyte indicator 106. In some embodiments, the sensor 100 may include a membrane covering at least a portion of the analyte indicator 106, and the one or more therapeutic agents may be incorporated within the membrane. In some embodiments, the one or more therapeutic agents include dexamethasone, triamcinolone, betamethasone, methylprednisolone, beclometasone, fludrocortisone, derivatives thereof, and analogs thereof, a glucocorticoid, an anti-inflammatory drug, e.g., a non-steroidal anti-inflammatory drug including but not limited to acetylsalicylic acid, isobutylphenylpropanoic acid.

Figure 4:
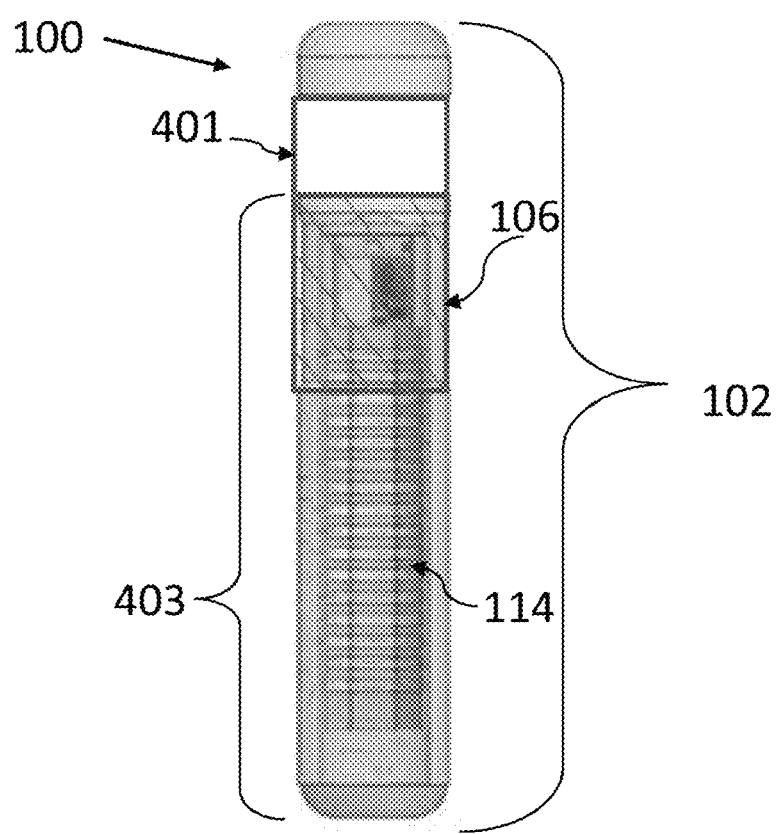
FIG. 4 is a schematic view illustrating a sensor embodying aspects of the present invention.

FIG. 4 is a schematic view of a sensor 100 embodying aspects of the present invention. In some non-limiting aspects, as shown in FIG. 4, the sensor 100 may include a drug eluting region 401 covering at least a portion of the sensor housing 102. In some non-limiting aspects, as shown in FIG. 4, the sensor 100 may include an analyte indicator 106. In some embodiments, the analyte indicator 106 may include a hydrogel co-polymerized with, carrying, or entrapping one or more optical signal stabilizing additives. In some non-limiting aspects, as shown in FIG. 4, the sensor 100 may include sensor electronic components, which may include any of the electronic components described in the present disclosure, including in FIG. 1 and FIG. 3 (e.g., the light source 108, the one or more photodetectors 110, the inductive element 114, and/or the one or more capacitors 118), as well as those described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. In some non-limiting aspects, as shown in FIG. 4, the sensor 100 may include an antioxidant coating 403 covering at least a portion of the sensor housing 102. In some non-limiting aspects, the antioxidant coating 403 may include one or more metals selected from Cu, W, Pt, Fe, Mo, Co, oxides, alloys, and complexes thereof. In some non-limiting aspects, the metal coating 403 may be coated on the hydrogel co-polymerized with, carrying, or entrapping one or more optical signal stabilizing additives.

The applicants have found, through repeated testing, that the opacity of an opaque polymer graft (e.g., a polymer graph that is translucent and/or cloudy) tends to vary during the time the sensor is placed within the living animal. This variation in the opacity may be caused by changes in the composition of the medium (e.g., interstitial fluid) around the sensor 100. These changes may be, for example, changes in protein concentration, fat concentration, temperature, volume, and/or number of cells in the medium. The variation in the opacity may be, for example, dynamic—from analyte measurement to analyte measurement (e.g., minute to minute). The variation in opacity may additionally or alternatively be dynamic over time (e.g., from day to day).

Variation in the opacity of an opaque polymer graft may disrupt analyte readings. In particular, when a polymer graft is opaque (i.e., cloudy), excitation light 329 emitted from the light source 108 in the sensor 100 may reflect off of the polymer graft/hydrogel and may be absorbed by the one or more photodetectors 110. As the opacity varies and the polymer graft/hydrogel becomes less opaque (i.e., more clear), more excitation light 329 may pass through the polymer graft/hydrogel. As a result, less excitation light 329 may be reflected off the polymer graft/hydrogel and onto the one or more photodetectors 110. Further, less fluorescent light 331 may also be reflected off the polymer graft and absorbed by one or more of the photodetectors 110. Thus, the variation in the opacity may cause a change in the output of the one or more photodetectors 110, and this change may be unrelated to the amount of analyte in the medium.

Figure 5:
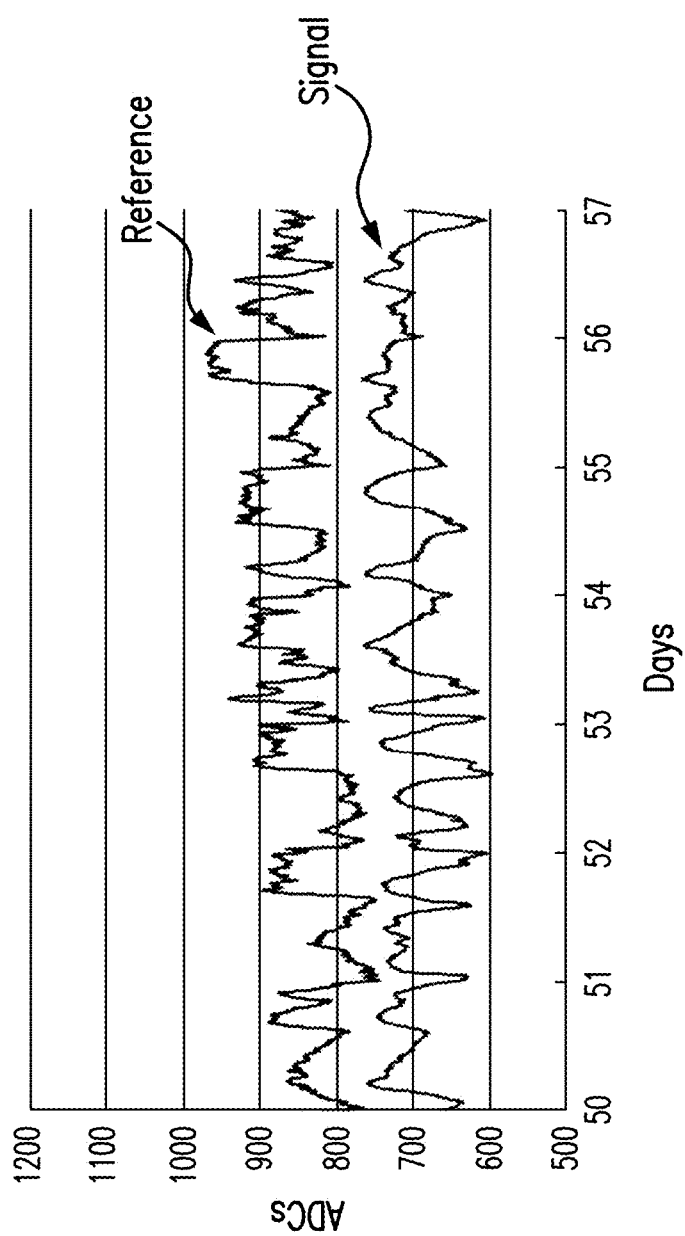
FIG. 5 is a graph showing the temperature-corrected signal and reference readings (analog to digital conversion) over time from a sensor that lacks optical signal stabilizing additives.
Figure 6:
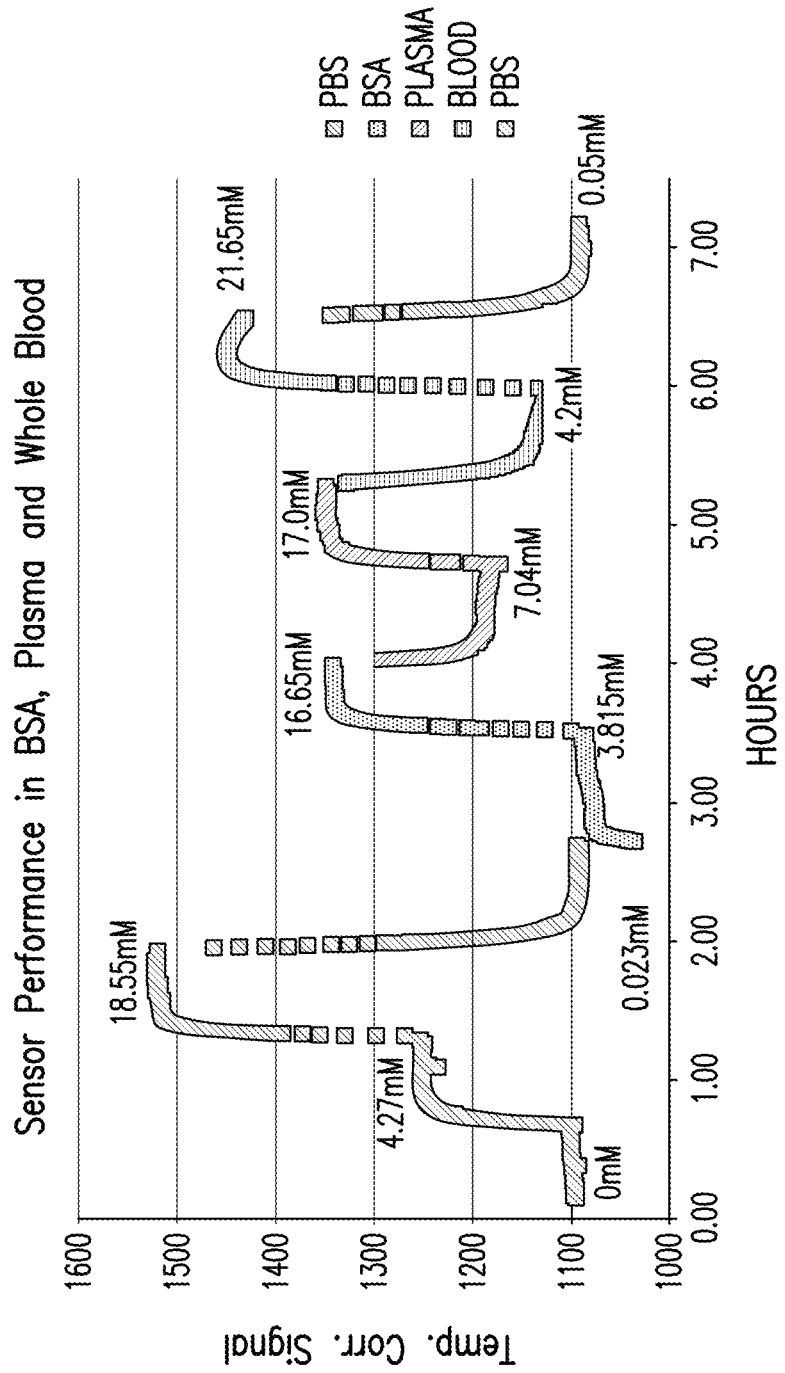
FIG. 6 is a graph showing the temperature-corrected signal of a sensor that lacks optical signal stabilizing additives over time from a sensor in various environments starting with phosphate buffered saline (PBS), followed by bovine serum albumin (BSA) in phosphate buffered saline, plasma, whole blood, and PBS.

An example of the temperature-corrected signal and reference readings from a sensor that lacks the one or more optical signal stabilizing additives of the present disclosure is shown in FIG. 5. The instability in the signal may point to optical changes in the hydrogel which in turn alters the quantum efficiency of fluorescence of the anthracene-based fluorescent moiety and thus alters the signal interpretation based on that level of optical change. A series of biological fluids that are each present in the subcutaneous tissues of humans were tested and the results of the signal output showed that the quantum efficiency is altered when each of the various fluids is present around the sensor as shown in FIG. 6. As shown in FIG. 6, the presence of each of bovine serum albumin (BSA) in phosphate buffered saline, plasma, and whole blood caused signal instability. Other biological substances such as fatty acids, lipids, and other biological media may also alter signal output.

Error may be introduced in the analyte readings as the opacity of the polymer graft/hydrogel changes. When opacity is at an increased level, there may be an increase in the amount of excitation light 329 or fluorescent light 331 absorbed into the polymer graft/hydrogel and then reflected back into the one or more photodetectors 110. However, when the hydrogel is less opaque and clearer in nature, there may be a decrease in the amount of excitation light 329 or fluorescent light 331 absorbed by the one or more photodetectors 110. When the polymer graft/hydrogel is opaque, there may be no way to distinguish whether a higher analyte reading is due to (a) more light being absorbed by the photodiodes because of opacity or (b) an actual increase in concentration of the analyte (e.g., glucose) in the medium (e.g., ISF).

Accordingly, in some embodiments, the analyte indicator 106 may be configured to have little or no variation in opacity during the time in which the sensor 100 is placed within the living animal (e.g., with protein infiltration) and, thus, may reduce the corresponding error in analyte readings. In other words, in some embodiments, because the variation of the analyte indicator 106 is reduced, the change in the photodetector output caused by the opacity variation may be reduced. In some non-limiting embodiments, the sensor 100 may be configured to be placed within the living animal for at least one day, one week, two weeks, one month, two months, six months, one year, or longer. In some non-limiting embodiments, the analyte indicator 106 may be configured to pass a percentage of light (e.g., 70%) and may be configured such that the percentage of light allowed to pass through the analyte indicator 106 does not change by more than a certain percentage (e.g., 50%, 30%, 20%, 10%, 5%, 2%, or 1%) for at least the duration of the time for which the sensor 100 is configured to be placed within the living animal (e.g., one day, one week, two weeks, one month, two months, three months, six months, one year, or longer). In some embodiments, the analyte indicator 106 may be clear. In some alternative embodiments, the analyte indicator 106 may be opaque (i.e., translucent and/or cloudy).

In some embodiments, the analyte indicator 106 may be configured such that variation of the opacity of the polymer graft during measurement of the analyte in the medium within the living animal is small or non-existent. As a result, the variation in the opacity may cause not more than a small change, which is unrelated to the amount of analyte in the medium, in the measurement signal output by a photodetector (e.g., photodetector 224). In some non-limiting embodiments, the change in the measurement signal caused by the variation of the opacity of the analyte indicator 106 may be, for example, 20% or less, 15% or less, 10% or less, 5% or less, 2% or less, 1% or less, or 0.5% or less.

In some non-limiting embodiments, the percentage of light allowed to pass through the analyte indicator 106 does not change by more than a percentage within a range of 0% to 50%, and this range of percentages should be understood as describing and disclosing all percentages (including all decimal or fractional percentage numbers) within this range. In some non-limiting embodiments, variation in the opacity of the analyte indicator 106 does not cause a change in a measurement signal output by a photodetector of more than a percentage within a range of 0% to 20%, and this range of percentages should be understood as describing and disclosing all percentages (including all decimal or fractional percentage numbers) within this range.

In some embodiments, the analyte indicator 106 has acceptably fast analyte response time and an acceptable analyte responsivity. Analyte response time is the amount of time needed for the indicator molecules 104 in the analyte indicator 106 to respond (e.g., change an optical characteristic) to a change in glucose concentration. Whether an analyte response time is acceptably fast is use dependent. For example, in the context of a polymer graft in a sensor placed in a human and used for in vivo measurement of changes in glucose concentration in interstitial fluid, an analyte response time may be acceptably fast when fast enough to detect a hypoglycemic or hyperglycemic event and allow time for the human to respond appropriately. In some embodiments, the analyte indicator 106 may have an analyte response time less than 15 minutes. In one non-limiting embodiment, the analyte indicator 106 may have an analyte response time of less than 10 minutes. In another non-limiting embodiment, the analyte indicator 106 may have an analyte response time of less than 5 minutes.

Analyte responsivity is the degree to which indicator molecules 104 in the analyte indicator 106 respond (e.g., change an optical characteristic) to a change in glucose concentration. Analyte responsivity may be acceptable when the response produces a measurable change (e.g., when a change in the amount of light 331 emitted by the indicator molecules 104 of the analyte indicator 106 is sufficient to measurably change the signal output by the signal photodetector 224).

In some non-limiting embodiments, the one or more optical signal stabilizing additives may be provided in the analyte indicator 106 (e.g., hydrogel) of the analyte sensor 100. In some non-limiting embodiments, one or more optical signal stabilizing additives may be incorporated into the analyte indicator 106 by mixing, entrapping or polymerizing the one or more optical signal stabilizing additives with indicator monomer and one or more acrylate monomers. In some non-limiting embodiments, one or more optical signal stabilizing additives may be provided as co-monomers of four monomers according to Formula V: A-B-C-D [Formula V], wherein A is an indicator monomer, B is a methacrylate monomer, C is a polyethylene glycol monomer, and D is a compound of one or more optical signal stabilizing additives, wherein A is 0.001 to 10% by weight, B is 1 to 99% by weight, C is 1 to 99% by weight, and D is 0.001 to 99% by weight of the total polymer. In some aspects, A is 0.01 to 10% by weight, B is 1 to 99% by weight, C is 1 to 99% by weight, and D is 0.01 to 99% by weight of the total polymer.

In one non-limiting embodiment, the analyte indicator 106 may contain: (i) the TFM fluorescent indicator; (ii) hydroxyethylmethacrylate (HEMA), which is a methacrylate; (iii) polyethylene glycol (PEG); and (iv) one or more optical signal stabilizing additives of the present disclosure. In some embodiments, the PEG may be polyethylene glycol methacrylate (PEG-methacrylate) or polyethylene glycol diacrylate (PEG-diacrylate or PEGDA). In one aspect, monomers (i)-(iii) may be in specific molar ratios.

In some non-limiting embodiments, the analyte indicator 106 may contain four monomers: (i) the TFM fluorescent indicator; (ii) hydroxyethylmethacrylate (HEMA), which is a methacrylate; (iii) polyethylene glycol (PEG); and (iv) one or more optical signal stabilizing additives. In some embodiments, the PEG may be polyethylene glycol methacrylate (PEG-methacrylate) or polyethylene glycol diacrylate (PEG-diacrylate or PEGDA), and the one or more optical signal stabilizing additives may be two or more optical signal stabilizing additives. In some embodiments, the four monomers may be in specific molar ratios. For example, in some non-limiting embodiments in which the analyte indicator 106 is opaque, the analyte indicator 106 may comprise 0.001 to 10 molar percent, HEMA may comprise 10 to 90 molar percent, PEGDA may comprise 10 to 90 molar percent, and the one or more optical signal stabilizing additives may comprise 0.001 to 90 molar percent. With this formulation, the combined (i.e., total) monomers may, in one example, be 30% by volume of the polymerization solution used for the polymerization reaction with the remainder of the polymerization solution being water (i.e., the polymerization solution may be 70% water by volume). For another example, in one non-limiting embodiment, the analyte indicator 106 may be made using a polymer solution that is 50% water by volume and 50% monomers by volume.

In some embodiments, the relative molar percent of the one or more optical signal stabilizing additives may be within a specific range. In some embodiments, the relative molar percent of the compound of one or more optical signal stabilizing additives ranges between 0.1 and 100, 10 to 90, 20 to 80, 30 to 70, 40 to 60, 5, 10, 15, 20, 25, 30, 35, 40, 45, 50 molar percent, or any number or range within the recited ranges. If the relative molar percent of the compound of the one or more optical signal stabilizing additives is greater than this range, the hydrogel is not formed. If the relative molar percent of the compound of the one or more optical signal stabilizing additives is lower than this range, the unexpected longevity and functionality-boosting effects described in this disclosure may not be obtained.

In some aspects, the one or more optical signal stabilizing additives may include but are not limited to titanium dioxide ($TiO_2$), barium sulfate, magnesium silicate, hollow microspheres (beads), solid microspheres (beads), monomers having vinyl functionality, dopants containing dithio groups. In some aspects the one or more optical signal stabilizing additives may have particle sizes, e.g., D50, ranging from about 0.001 to about 100 μm, about 0.01 to about 60 μm, about 0.05 to about 50 μm, about 0.1 to about 40 μm, about 0.5 to about 30 μm, about 1 to about 25 μm, about 5 to about 15 μm, or any number or range within any combination of the recited ranges. Particle sizes may be determined according to any suitable particle size analyzer.

In some aspects, hollow or solid beads are composed of silicon dioxide, glass, alumina, melamine, polystyrene or polystyrene functionalized with one or more polyethylene glycols (PEGs), amino-, carboxy-sulfate, sulfate, carboxylate, and hydroxylate moieties. In some aspects, monomers having vinyl functionality may include, but are not limited to one or more of hydroxybutyl methacrylate, cyclohexyl methacrylate, hydroxypropyl methacrylate, vinyl acetate, and various other hydrophobic vinyl monomers. In some aspects, dopants may include, but are not limited to 3,3'-dithiodipropionic acid and other dithio-containing compounds ranging in alkyl chain length from 2-34 carbon atoms.

As an example of an opaque polymer graft, in a non-limiting embodiment, the fluorescent indicator may comprise 0.01-10 molar percent, HEMA may comprise 80-99 molar percent, and PEGDA may comprise 2-10 molar percent. With this formulation, the combined (i.e., total) monomers may, in one example, be 30% by volume of the polymerization solution used for the polymerization reaction with the remainder of the polymerization solution being water (i.e., the polymerization solution may be 70% water and other components by volume). For another example, in one non-limiting embodiment, the analyte indicator 106 may be made using a polymer solution that is 50% water by volume and 50% monomers by volume, where the TFM fluorescent indicator, HEMA, and PEGDA may comprise about 0.1 to about 0.5 molar percent, about 90 to about 98 molar percent, and about 4 to about 6 molar percent, respectively, of the monomers in the solution.

In some aspects, the one or more optical signal stabilizing additives of the present disclosure are present at a concentration of about 1 to about 1000 mg/ml, about 5 mg/ml to about 500 mg/ml, about 10 mg/ml to about 250 mg/ml, about 20 mg/ml to about 100 mg/ml, about 25 mg/ml to about 75 mg/ml, about 30 mg/ml to about 60 mg/ml of the analyte indicator 106, or any other number or range within any of the recited ranges.

The PEGDA may act as a cross-linker and create a sponge-like matrix/hydrogel. In some non-limiting embodiments, the PEG-containing graft/hydrogel may become clear if a sufficient amount of additional PEG is added to the mixture (i.e., if it is fabricated with a higher concentration of PEG), and a clear analyte indicator 106 may be made from such a formulation. For example, in one non-limiting embodiment, the analyte indicator 106 may be made using a polymer solution that is 50-60% water by volume and 40-50% monomers by volume, where the TFM fluorescent indicator, HEMA, and PEG-methacrylate may comprise 0.1 molar percent, 49.9 molar percent, and 50 molar percent, respectively, of the monomers in the solution. In some embodiments, the polymer graft may be synthesized using conventional free radical polymerization.

In some alternative embodiments, a clear analyte indicator 106 may be made by substituting acrylic acid for the PEG. With low concentrations of acrylic acid, this composition may be opaque, and the opacity may vary over time. However, similar to PEG, at higher concentrations of acrylic acid, the polymer graft/hydrogel becomes clear. For example, in one non-limiting embodiment, the analyte indicator 106 may be made using a polymer solution that is 55% water by volume and 45% monomers by volume, where the fluorescent indicator, HEMA, PEGDA, and acrylic acid may comprise about 0.01 to about 5 molar percent, about 80 to about 85 molar percent, about 0.01 to about 1 molar percent, and about 15 to about 20 molar percent, respectively, of the monomers in the solution. In some embodiments, an analyte indicator 106 made with acrylic acid may have mechanical properties superior to a polymer graft not made with acrylic acid. For example, in one non-limiting embodiment, the analyte indicator 106 made with acrylic acid may be less brittle and may remain elastic.

In some other alternative embodiments, a clear analyte indicator 106 may be formed using relatively high total concentrations of both acrylic acid and PEG. For example, in one non-limiting embodiment, the analyte indicator 106 may be made using a polymer solution that is 50% water by volume and 50% monomers by volume, where the fluorescent indicator, HEMA, PEGDA, and acrylic acid may comprise 0.1 molar percent, 79.45 molar percent, 2.45 molar percent, and 18 molar percent, respectively, of the monomers in the solution. For another example, in one non-limiting embodiment, the analyte indicator 106 may be made using a polymer solution that is 50% water by volume and 50% monomers by volume, where the fluorescent indicator, HEMA, PEGDA, and acrylic acid may comprise 0.1 molar percent, 83.68 molar percent, 2.45 molar percent, and 13.77 molar percent, respectively, of the monomers in the solution. By incorporating a higher percentage of acrylic acid instead of (or in addition to) PEG, the graft 106 may be much less opaque, and the opacity may not change over time. This may improve accuracy in measurements of analyte concentrations as changes in opacity affect the readings.

In embodiments that use acrylic acid to form the analyte indicator 106, opacity may not change and analyte readings may be unaffected.

When the opacity of the analyte indicator 106 remains the same over time, the amount of light received by the photodetector(s) 110 from the analyte indicator 106 may not fluctuate as often as when opacity changes. Therefore, the amount of light received by the photodetector(s) 110 from the analyte indicator 106 may be based solely on the level of analyte (e.g., glucose) in the medium, not opacity.

EXAMPLE

Figure 7:
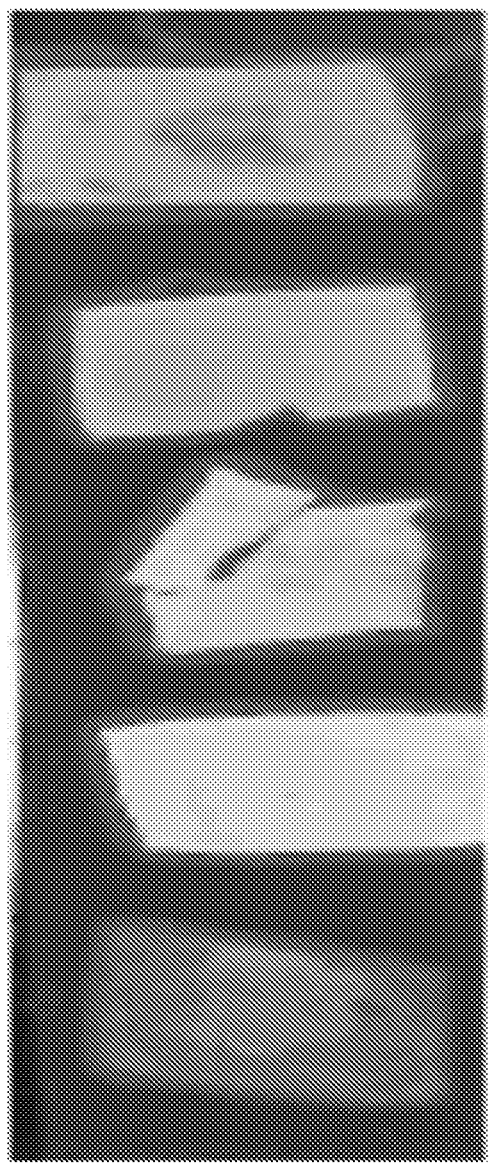
FIG. 7 provides images of hydrogel slabs with varying concentrations of TiO$_2$: From left to right: control (no TiO$_2$), 100 mg/mL, 75, 50, and 25 mg/mL TiO$_2$.

Hydrogels (both slab gels and grafted cores) containing optical signal stabilizing additives were polymerized. Response to glucose and whiteness of the gels were evaluated to assess the effect of the additives. Hydrogels containing $TiO_2$ dried white, whereas hydrogel with no $TiO_2$ dried clear, which suggests that the addition of $TiO_2$ affords stability in opacity even in suboptimal hydration conditions, as shown in FIG. 7. In FIG. 7, hydrogel slabs with varying concentrations of $TiO_2$ were tested (From left to right: control (no $TiO_2$), 100 mg/mL, 75, 50, 25 mg/mL).

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although in some embodiments, the analyte sensor 100 may be an optical sensor, this is not required, and, in one or more alternative embodiments, the analyte sensor may be a different type of analyte sensor, such as, for example, an electrochemical sensor, a diffusion sensor, or a pressure sensor. Also, although in some embodiments, the analyte sensor 100 may be an implantable sensor, this is not required, and, in some alternative embodiments, the analyte sensor may be a transcutaneous sensor having a wired connection to an external transceiver. For example, in some alternative embodiments, the analyte sensor 100 may be located in or on a transcutaneous needle (e.g., at the tip thereof). In these embodiments, instead of wirelessly communication using an antenna (e.g., inductive element 114), the analyte sensor may communicate with the external transceiver using one or more wires connected between the external transceiver and a transceiver transcutaneous needle including the analyte sensor. For another example, in some alternative embodiments, the analyte sensor may be located in a catheter (e.g., for intravenous blood glucose monitoring) and may communicate (wirelessly or using wires) with an external transceiver.

What is claimed is:

1. A sensor for measurement of an analyte in a medium within a living animal, the sensor comprising:
   an analyte indicator having an opacity; and
   one or more optical signal stabilizing additives, wherein the one or more optical signal stabilizing additives maintain the opacity of the analyte indicator over time.

2. The sensor of claim 1, wherein the one or more optical signal stabilizing additives are selected from one or more of a)-g):
   a) titanium dioxide ($TiO_2$);
   b) barium sulfate;
   c) magnesium silicate;
   d) hollow beads;
   e) solid beads;
   f) monomers having vinyl functionality; and
   g) dopants containing dithio groups.

3. The sensor of claim 1, wherein the one or more optical signal stabilizing additives have particle sizes of about 0.001 to about 100 μm.

4. The sensor of claim 1, wherein the one or more optical signal stabilizing additives include hollow or solid beads.

5. The sensor of claim 4, wherein the hollow or solid beads are composed of one or more of:
   a) silicon dioxide;
   b) glass;
   c) alumina;
   d) melamine; and
   e) polystyrene or polystyrene functionalized with one or more polyethylene glycols (PEGs), amino, carboxysulfate, sulfate, carboxylate, and hydroxylate moieties.

6. The sensor of claim 1, wherein the one or more optical signal stabilizing additives include monomers having vinyl functionality.

7. The sensor of claim 6, wherein the monomers having vinyl functionality include hydrophobic vinyl monomers.

8. The sensor of claim 6, wherein the monomers having vinyl functionality include one or more of hydroxybutyl methacrylate, cyclohexyl methacrylate, hydroxypropyl methacrylate, and vinyl acetate.

9. The sensor of claim 1, wherein the one or more optical signal stabilizing additives include 3,3'-dithiodipropionic acid.

10. The sensor of claim 1, further comprising a sensor housing, wherein the analyte indicator covers at least a portion of the sensor housing.

11. The sensor of claim 1, further comprising a sensor substrate or a sensor electrode, wherein the analyte indicator covers at least a portion of the sensor substrate or the sensor electrode.

12. The sensor of claim 1, wherein the one or more optical signal stabilizing additives are co-monomers with the analyte indicator.

13. The sensor of claim 1, wherein the one or more optical signal stabilizing additives are co-monomers with the analyte indicator in a hydrogel.

14. The sensor of claim 1, wherein the one or more optical signal stabilizing additives are entrapped in a hydrogel covering at least a portion of the sensor housing.

15. The sensor of claim 1, wherein the analyte indicator comprises a polymer comprising co-monomers of four monomers according to Formula V: A-B-C-D [Formula V], wherein A is an analyte indicator monomer, B is a methacrylate monomer, C is a polyethylene glycol monomer, and D is an optical signal stabilizing additive, wherein A is 0.01 to 10% by weight, B is 1 to 99% by weight, C is 1 to 99% by weight, and D is 0.01 to 99% by weight of the total polymer.

16. The sensor of claim 1, wherein the analyte indicator is configured to pass a percentage of light, and the percentage of light passing through the analyte indicator would not change by more than 50% when the sensor is placed within the living animal for at least one month.

17. The sensor of claim 1, wherein the analyte indicator is configured to pass a percentage of light, and the percentage of light passing through the analyte indicator would not change by more than 20% when the sensor is placed within the living animal for at least one month.

18. The sensor of claim 1, wherein the analyte indicator is configured to pass a percentage of light, and the percentage of light passing through the analyte indicator would not change by more than 10% when the sensor is placed within the living animal for at least one month.

19. The sensor of claim 1, wherein the analyte indicator is configured to pass a percentage of light, and the percentage of light passing through the analyte indicator would not change by more than 50% when the sensor is placed within the living animal for at least two months.

20. The sensor of claim 1, wherein the analyte indicator is configured to pass a percentage of light, and the percentage of light passing through the analyte indicator would not change by more than 50% when the sensor is placed within the living animal for at least six months.

21. The sensor of claim 1, wherein the analyte indicator is a polymer hydrogel including acrylic acid.

22. The sensor of claim 1, wherein the analyte indicator comprises polyethylene glycol monomers.

23. The sensor of claim 1, wherein the analyte indicator is made of a polymer hydrogel including polyethylene glycol monomers.

24. The sensor of claim 1, wherein the one or more optical signal stabilizing additives comprise titanium dioxide.

25. The sensor of claim 1, wherein the one or more optical signal stabilizing additives comprise barium sulfate.

26. The sensor of claim 1, wherein the one or more optical signal stabilizing additives comprise magnesium silicate.

27. The sensor of claim 1, wherein the one or more optical signal stabilizing additives comprise hollow beads.

28. The sensor of claim 1, wherein the one or more optical signal stabilizing additives comprise solid beads.

29. The sensor of claim 1, wherein the one or more optical signal stabilizing additives comprise monomers having vinyl functionality.

30. The sensor of claim 1, wherein the one or more optical signal stabilizing additives comprise dopants containing dithio groups.

31. A sensor for measurement of an analyte in a medium within a living animal, the sensor comprising:
    an analyte indicator having an opacity; and
    one or more optical signal stabilizing additives, wherein the one or more optical signal stabilizing additives maintain the opacity of the analyte indicator over time, wherein the one or more optical signal stabilizing additives include one or more dithio-containing dopants ranging in alkyl chain length from 2-34 carbon atoms.

32. A method of fabricating a sensor for measurement of an analyte in a medium within a living animal, the method comprising:
    applying an analyte indicator having an opacity to a sensor such that the applied analyte indicator covers at least a portion of a sensor housing, sensor substrate, or sensor electrode, wherein the analyte indicator comprises one or more optical signal stabilizing additives, and the one or more optical signal stabilizing additives maintain the opacity of the analyte indicator over time.

33. The method of claim 32, wherein the one or more optical signal stabilizing additives are hollow or solid beads.

34. The method of claim 26, wherein the hollow or solid beads are composed of one or more of:
    a) silicon dioxide;
    b) glass;
    c) alumina;
    d) melamine; and
    e) polystyrene or polystyrene functionalized with one or more polyethylene glycols (PEGs), amino, carboxysulfate, sulfate, carboxylate, and hydroxylate moieties.

35. The method of claim 32, wherein the one or more optical signal stabilizing additives include monomers having vinyl functionality.

36. The method of claim 35, wherein the monomers having vinyl functionality include hydrophobic vinyl monomers.

37. The method of claim 35, wherein the monomers having vinyl functionality include one or more of hydroxybutyl methacrylate, cyclohexyl methacrylate, hydroxypropyl methacrylate, and vinyl acetate.

38. The method of claim 32, wherein the one or more optical signal stabilizing additives include one or more dithio-containing dopants ranging in alkyl chain length from 2-34 carbon atoms.

39. The method of claim 32, wherein the one or more optical signal stabilizing additives include 3,3'-dithiodipropionic acid.

* * * * *